US 6,560,477 B1

(12) United States Patent
Filler

(10) Patent No.: US 6,560,477 B1
(45) Date of Patent: May 6, 2003

(54) JOINT IMAGING SYSTEM UTILIZING MAGNETIC RESONANCE IMAGING AND ASSOCIATED METHODS

(75) Inventor: Aaron G. Filler, Santa Monica, CA (US)

(73) Assignee: The Regents of the University of California, Oakland, CA (US)

( * ) Notice: Subject to any disclaimer, the term of this patent is extended or adjusted under 35 U.S.C. 154(b) by 212 days.

(21) Appl. No.: 09/809,383

(22) Filed: Mar. 15, 2001

Related U.S. Application Data

(60) Provisional application No. 60/190,015, filed on Mar. 17, 2000.

(51) Int. Cl.[7] .............................................. A61B 5/055
(52) U.S. Cl. ...................................... 600/410; 324/309
(58) Field of Search ................................ 600/410, 411, 600/9; 324/307, 309, 300, 310, 318

(56) References Cited

U.S. PATENT DOCUMENTS

| | | | | |
|---|---|---|---|---|
| 4,843,322 A | | 6/1989 | Glover | 324/309 |
| 4,868,501 A | | 9/1989 | Conolly | 324/309 |
| 4,901,020 A | | 2/1990 | Ladebeck et al. | 324/309 |
| 5,541,515 A | * | 7/1996 | Tsujita | 600/415 |
| 5,560,360 A | | 10/1996 | Filler et al. | 128/653.2 |
| 5,706,813 A | | 1/1998 | Filler et al. | 128/653.5 |
| 5,748,801 A | * | 5/1998 | Goto | 382/270 |
| 6,169,817 B1 | * | 1/2001 | Parker et al. | 382/131 |
| 6,206,927 B1 | * | 3/2001 | Fell et al. | 623/20.29 |

FOREIGN PATENT DOCUMENTS

| | | | |
|---|---|---|---|
| GB | 0 640 350 A2 | 1/1995 | |
| JP | 2000-139870 | * 5/2000 | A61B/5/055 |

OTHER PUBLICATIONS

Atlas et al.; Nov. 1988; *STIR MR Imaging of the Orbit*; AJR 151:1025–1030.
Bydder et al.; (1992); *Comparison of FLAIR Pulse Sequences with Heavily T2 Weighted SE Sequences in MR Imaging of the Brain*; 185 Radiology Supp. 151.
Haase et al.; Apr. 1985; *H NMR chemical shift selective (chess) imaging*; Physics in Medicine & Biology, vol. 30, No. 4, pp. 341–344.
Dixon, T.; Oct. 1984; *Simple Proton Spectroscopic Imaging*; Radiology, vol. 153, No. 1, pp. 189–194.

* cited by examiner

Primary Examiner—Hieu T. Vo
(74) Attorney, Agent, or Firm—Greenberg Traurig, LLP

(57) ABSTRACT

A method and apparatus utilized for imaging joint regions are disclosed which utilize blood pool contrast agents and particular magnetic resonance imaging parameters, including fat-suppression, to obtain medically useful images of joints. In particular, the methods and apparatus provide medical personnel with accurate and detailed joint images, including joint spaces, which are useful for various therapeutic and diagnostic applications.

40 Claims, 2 Drawing Sheets

JOINT IMAGING SYSTEM UTILIZING MAGNETIC RESONANCE IMAGING AND ASSOCIATED METHODS

CROSS-REFERENCES

This application claims priority from Provisional Application Serial No. 60/190,015, filed Mar. 17, 2000, entitled "Enhanced Nerve Imaging with Ferrite Contrast Agents," naming Aaron G. Filler as inventor, the contents of which are hereby incorporated in their entirety by this reference.

FIELD OF THE INVENTION

The present invention relates generally to the field of imaging and, more particularly, to the utilization of magnetic resonance imaging to image joint spaces.

BACKGROUND OF THE INVENTION

Previous techniques utilized to image internal structures of interest in subjects are well known in the art. Generally, prior art techniques utilize computed axial tomographic X-rays, also known as CT scanning, or magnetic resonance imaging (MRI) to afford an internal view of particular regions in subjects undergoing imaging procedures. These prior art techniques may be adequate for image construction of tissue matter such as bone, muscle, brain, spinal cord, veins, arteries and nerves, as well as other tissues. However, particular regions of interest, namely the joint regions and spaces, are not as amenable to prior art techniques of imaging, particularly tissue selective imaging.

Joint spaces are found in such medically important sites as the knee joint, intervertebral discs, the shoulder joint and the hip joint, as well as other joints. These four listed joints, taken together, are the subject of various pathologies that affect millions of patients and require over one million surgical repair procedures each year in the United States.

Despite the enormous medical and economic impact of various joint diseases, there has not been any prior art methods that are amenable to generalized automated use for the imaging of joints that result in unobstructed images or three-dimensional views. Typically, the prior art techniques provide joint images wherein particular angles of viewing the joint are impeded or obstructed by bone, marrow, fat and blood vessels, for example. Prior art methods are typically comprised of operator driven techniques wherein the general image of the joint and surrounding tissue is observed and imaged. The operator then uses a computer-input device to outline and identify components of interest in the joint region in each of a series of successive image slices taken of the joint region. Surrounding tissues that are components of the joint region that are not necessarily of interest are then deleted and the remaining elements of the joint region, in the series of image slices, are computationally stacked and projected. As those skilled in the art can appreciate, this method is a painstakingly slow and subjective process.

The use of X-rays to evaluate joint regions is well known in the art. This typically entails the direct, invasive injection of joints of interests with various X-ray contrast materials. However, dense bone and the injected contrast material often display similar effects on the resultant X-ray image, and as a result, this technique is only of limited use. Further, the cartilage components of the joint may be difficult to view. Therefore, the need for novel and improved techniques and methods of joint imaging will be well appreciated by those skilled in the art of medical imaging.

One approach of particular interest that has been used to image physiological structures is magnetic resonance imaging (MRI). By way of introduction, MRI involves the exposure of tissue to a variety of different magnetic and radio-frequency (rf) electromagnetic fields. The response of the tissue's atomic nuclei to the fields is then processed to produce an image of the tissue.

More particularly, the tissue is initially exposed to a polarizing magnetic field. In the presence of this field, nuclei exhibiting magnetic moments (hereinafter referred to as spins) will seek to align themselves with the field. The nuclei precess about the polarizing field at an angular frequency (hereinafter referred to as the Larmor frequency) whose magnitude depends upon both the field's strength and the magnetogyric constant of the specific nuclear species involved.

Although the magnetic components of the spins cancel each other in a plane perpendicular to the polarizing field, the spins exhibit a net magnetic moment in the direction of the polarizing field. By applying an excitation field perpendicular to the polarizing field and at a frequency near the Larmor frequency, the net magnetic moment can be tilted. The tilted magnetic moment includes a transverse component, in the plane perpendicular to the polarizing field, rotating at the Larmor frequency. The extent to which the magnetic moment is tilted and, hence, the magnitude of the net transverse magnetic moment, depends upon the magnitude and duration of the excitation field.

An external return coil is used to sense the field associated with the transverse magnetic moment, once the excitation field is removed. The return coil, thus, produces a sinusoidal output, whose frequency is the Larmor frequency and whose amplitude is proportional to that of the transverse magnetic moment. With the excitation field removed, the net magnetic moment gradually reorients itself with the polarizing field. As a result, the amplitude of the return coil output decays exponentially with time.

Two factors influencing the rate of decay are known as the spin-lattice relaxation coefficient $T_1$ and the spin-spin relaxation coefficient $T_2$. The spin-spin relaxation coefficient $T_2$ represents the influence that interactions between spins have on decay, while the spin-lattice relaxation coefficient $T_1$ represents the influence that interactions between spins and fixed components have on decay. Thus, the rate at which the return coil output decays is dependent upon, and indicative of, the composition of the tissue.

By employing an excitation field that has a narrow frequency band, only a relatively narrow band within a nuclear species will be excited. As a result, the transverse magnetic component and, hence, return coil output, will exhibit a relatively narrow frequency band indicative of that band of the nuclear species. On the other hand, if the excitation field has a broad frequency band, the return coil output may include components associated with the transverse magnetic components of a greater variety of frequencies. A Fourier analysis of the output allows the different frequencies, which can be indicative of different chemical or biological environments, to be distinguished.

In the arrangement described above, the contribution of particular spins to the return coil output is not dependent upon their location within the tissue. As a result, while the frequency and decay of the output can be used to identify components of the tissue, the output does not indicate the location of components in the tissue.

To produce such a spatial image of the region of tissue, gradients are established in the polarizing field. The direction of the polarizing field remains the same, but its strength varies along the x, y, and z axes oriented with respect to the tissue. By varying the strength of the polarizing field linearly along the x-axis, the Larmor frequency of a particular nuclear species will also vary linearly as a function of its position along the x-axis. Similarly, with magnetic field gradients established along the y-axis and z-axis, the Larmor frequency of a particular species will vary linearly as a function of its position along these axes.

As noted above, by performing a Fourier analysis of the return coil's output, the frequency components of the output can be separated. With a narrow band excitation field applied to excite a select nuclear species, the position of a spin relative to the xyz coordinate system can then be determined by assessing the difference between the coil output frequency and the Larmor frequency for that species. Thus, the MRI system can be constructed to analyze frequency at a given point in time to determine the location of spins relative to the magnetic field gradients and to analyze the decay in frequency to determine the composition of the tissue region at a particular point.

The generation and sensing of the fields required for proper operation of an MRI system is achieved in response to the sequential operation of, for example, one or more main polarizing field coils, polarizing gradient field coils, rf excitation field coils, and return field coils. Commonly, the same coil arrangement is used to generate the excitation field and sense the return field. These rf coils, or antennas, can be of various prior art designs including, surface coils, solenoid coils or multi-coil arrays, such as phased arrays. A variety of different sequences have been developed to tailor specific aspects of MRI system operation, as described, for example, in U.S. Pat. No. 4,843,322 (Glover); U.S. Pat. No. 4,868,501 (Conolly); and U.S. Pat. No. 4,901,020 (Ladebeck et al.).

In order to enhance the utility of MRI systems in imaging various tissues, the administration of pharmaceutical agents is often used to enhance the contrast of particular tissues relative to the surrounding tissues in the images produced. These agents are referred to as contrast agents. Contrast agents act to change the relaxation or return output times of tissues in which they are localized.

A wide variety of contrast agents are known in the art. These are utilized according to the type of imaging to be performed as well as the particular tissue type undergoing the imaging procedures. For example, contrast agent types currently utilized include gastrointestinal, tumor specific as well as intravascular or blood pool agents.

As mentioned previously, although the use of MRI and its various permutations have been successfully utilized to construct images of many tissue and organ types, the production of useful tissue selective images of joint spaces has presented some difficulty. This difficulty in imaging is due to the fact that joint regions are comprised of multiple components including, for example, blood, joint fluids, muscles, tendons, cartilage, fat, bone and the marrow incorporated within the bone. As a result, for effectively every type of magnetic resonance pulse imaging sequence, various component tissues, singly or in combination, result in bright signals in the resultant image. Consequently, prior art methodologies of imaging, in two and three-dimensions, of joint spaces utilizing MRI can be improved upon, wherein particular protocols, herein disclosed, are employed comprising particular pulse sequences in combination with contrast agents resulting in informative images of joint regions and spaces which are unobstructed by various other joint components, such as blood vessels, bone, and marrow for example.

Accordingly, the objective of the present invention is to provide a method that overcomes the previously mentioned obstacles to imaging joints utilizing MRI. More particularly, a method is disclosed whereby components of joint regions, particularly bone and the marrow components incorporated within, are selectively removed singly or in any combination with other components comprising the joint region. This effect of removing bone and marrow contributions to joint images utilizing MRI will be referred to as the "black bone" effect. When put into practice, the method disclosed herein will result in the production of previously unavailable, medically useful images of joint spaces.

It is an additional object of the present invention to provide generalized, automated methods of joint space imaging construction that can performed expeditiously and utilized in conjunction with other various MRI imaging techniques that result in the useful imaging of joint regions.

SUMMARY OF THE INVENTION

These and other objects are achieved by the methods herein disclosed for imaging joint spaces utilizing magnetic resonance imaging. Such regions of interest, or joint spaces, are typically those joint spaces found in vertebrate animals, including, but not limited to, humans, pigs, mice, horses.and the plethora of other vertebrates too numerous to list. More particularly, joint spaces are points of articulation between two or more bones, especially such a connection that allows motion. These images are generated efficiently by utilizing a magnetic resonance scanner under disclosed conditions that remove bone and marrow signals from the resultant images as well as other joint region components if so desired.

In order to acquire clinically useful images of joint spaces, the subject, a vertebrate for example, undergoing the imaging procedures disclosed herein, is injected intravenously with a blood pool contrast agent composition. The blood pool contrast agent composition is allowed to circulate throughout the subject. Subsequently, the subject, now containing the blood pool contrast agent composition, is positioned into a magnetic resonance imaging apparatus so that the area of interest, in particular a joint region, is subjected to a magnetic polarizing field. The magnetic polarizing field may be in the range of about 0.1 to 5 Tesla, preferably about 0.25 to 1.5 Tesla.

Following this step, the joint region is subjected to a variety of specific radio-frequency (rf) electromagnetic field pulse sequences that result in the selective deletion and/or imaging of particular components of the joint region in the resulting images. For example, various fluids such as synovial fluid are found in particular joints such as knee joints and inter-vertebral joints, respectively. In order to suppress these joint components' contribution to the image, water suppression techniques can be used, as detailed below. Similarly, the methods disclosed herein may be utilized to visualize cartilage, such as hydrated cartilage as well as Lumbar disks, for example.

The previously administered blood pool contrast agent composition is used in order to suppress the contribution of bone and marrow to the image as well as blood, if so desired. The area being imaged contains the blood pool contrast agent composition which is comprised of suitably configured components that allow for the uptake of this pharmaceutical into the reticuloendothelial system. It is by the careful consideration of size and composition of these blood pool contrast agents that this composition is cleared into bone marrow as well as being able to remaining in the bloodstream. Here, by employing the magnetic resonance imaging scanner to collect fat-suppressed, $T_2$-weighted images, in conjunction with the administration of the aforementioned blood pool contrast agent compositions, bone, marrow and fat are eliminated in the image. The image therefore displays the remaining joint space, and when combined with a series of consecutive joint space images taken under the same parameters, can be subjected to image data analysis. Such image data analysis can include various methods of computational three-dimensional projection/reconstruction, in order to provide unobstructed observation of the joint space from essentially any point of view. That is, the resultant three dimensional image may be rotated "virtually" to provide a view of the joint space from a desired point of view, unobstructed by bone, marrow, blood vessels and fat, for example.

Other features and advantages of the present invention will become apparent from the following detailed description, taken in conjunction with the accompanying figure, which illustrate by way of example the principles of the present invention.

DETAILED DESCRIPTION

The methods of magnetic resonance imaging of the present invention are designed for use in conjunction with a broader medical system whereby expeditious and accurate images of joint regions are produced. The system and associated methods disclosed herein allow joint images to be displayed as 2-dimensional, cross-sectional images as well as 3-dimensional reconstructions that provide "virtual" rotation of the joint region from any desired point of view. The images may selectively include or exclude other components or structures of the joint region and may illustrate the positional relationship of one or more of these components to the joint space imaged as well as relative to each other.

Figure 1:
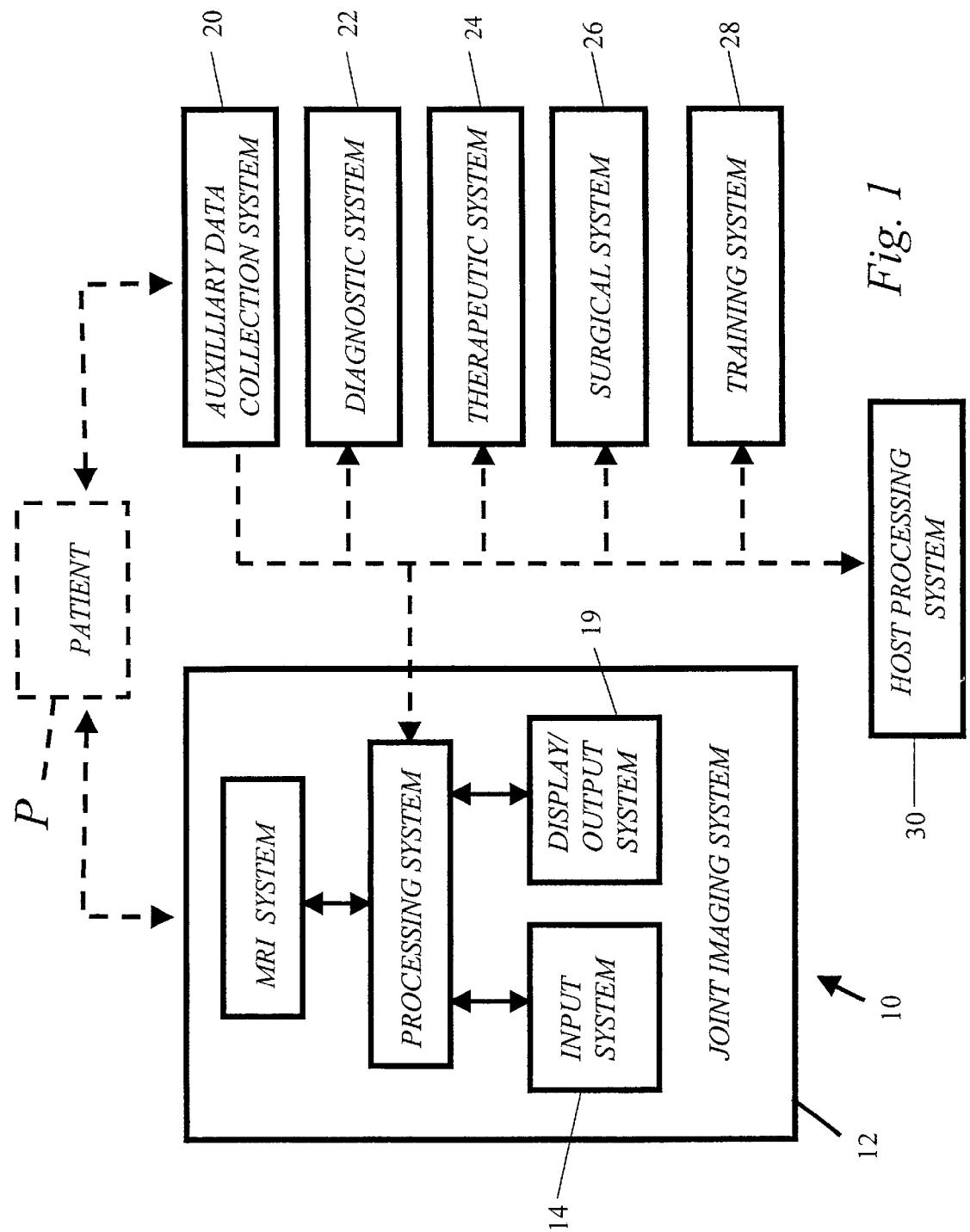
FIG. 1 is a diagram depicting the joint imaging system in accordance to the methods and teachings of the present invention which can be utilized in conjunction with other systems to provide enhanced joint images as well as feedback that will supplement diagnosis, therapy, surgery and training.

As shown in FIG. 1 the joint imaging system 12 included in medical system 10 includes four basic components: MRI system 18, processing system 16, input system 14, and output/display system 19. In the preferred arrangement, the MRI system 18 is a conventional MRI system modified for use in collecting image data of a patient P under examination. The processing system 16 responds to operator inputs applied via input system 14 to control MRI system 18 and process its output to display the resultant joint region at output/display system 19. As will be described in greater detail below, processing system 16 employs a variety of different imaging protocols, alone or in combination, to ensure that the images produced are of a quality heretofore unachieved.

The medical system 10 includes a number of components that supplement the imaging information produced by joint imaging system 12 and/or uses that information for a variety of purposes. For example, an auxiliary data collection system 20 may be included to collect image information about non-joint space structures, such as blood vessels and bone, in the imaged region of patient, P. This information can then be used to suppress and/or enhance the appearance of those structures in the joint region images produced by system 10.

A diagnostic system 22, included in system 10, may be used to analyze the images produced by system 12. Given the high resolution, detail, and accuracy of joint region images produced by system 12, diagnostic system 22 can be programmed to analyze joint region information to detect various pathologies, for example, disc joint compressions, neural compressions, injuries, and tumors. Diagnostic system 22 provides outputs indicative of the location of pathologies and may, by consultation with a database of image information associated with clinically assessed pathologies, provide an indication of the nature and magnitude of imaged pathologies. These outputs can be used for diagnosis, or applied as feedback to system 12 to refine a region of interest (ROI) under examination in patient P.

Medical system 10 may also include a therapeutic system 24 and surgical system 26. Systems 24 and 26 employ information about the patient's joint region structure from system 10 to assist in the proper administration of a desired therapeutic or surgical operation. For example, the information may be used to guide a robotic stylus to a damaged joint site for treatment or to allow an operation on various joint region structures to be performed without damage to other components of the patient's joint region. The systems 24 and 26 may operate independent of physician control or may simply provide the physician with real-time feedback concerning the relationship between an operation being performed and other proximate structures.

A training system 28 is included in the medical system 10 for a variety of different purposes. For example, the training system 28 may be used to demonstrate the anatomy of various joint region structures, along with their positional relationship to other patient structures. This information has great educational value given the extremely limited ability of prior art techniques, including direct examination, to provide detailed anatomical information. Training system 28 may also be designed to analyze the effectiveness of joint imaging system 12 and provide feedback used to control the pulse sequences and other operational parameters of joint imaging system 12.

As one final component, medical system 10 may include a host processing system 30 in addition to, or in place of, separate processing systems in the other components of system 10. Although not separately shown in FIG. 1, host-processing system 30 includes a central processing unit (CPU) coupled to the remainder of system 10 by input/output circuits. Memory is provided to store software instructions, used to control the operation of the CPU and, hence, the various components of system 10, and to store image and other data collected by system 10. The use of separate host processing system 30 is particularly desirable where various components of system 10 are to be operated in interactive fashion pursuant to a single set of software instructions.

In order to enhance the quality of the images produced by MRI techniques, the use of contrast agent compositions is often employed. Contrast agents generally are comprised of ions that have a large number of unpaired electrons. As a result, contrast agents have larger magnetic moments than the surrounding protons in an area undergoing magnetic resonance imaging and are therefore useful to medical personnel because of their enhancement of local magnetic fluctuating magnetic fields. The administration of contrast agent compositions provides an improvement in contrast in the resultant images and a more accurate view of internal structures.

The present invention utilizes contrast agents in conjunction with MRI in order to improve the visualization of joint regions. In accordance with the teachings of the present invention, contrast agent compositions that may be utilized include superparamagnetic as well as diamagnetic contrast agent compositions. Non-limiting examples of superparamagnetic contrast agent compositions include ferrous hydroxides and ferromagnetic hemotites. Diamagnetic contrast agent compositions can include dysprosium-DOTA poly lysine example, as well as others.

As previously mentioned, effectively every type of magnetic resonance pulse sequencing imaging method results in various tissues near or around joint spaces giving off bright signals. By utilizing contrast agent compositions, particularly of the blood pool type, as one component of the herein disclosed method, the present invention provides a method by which previously unachieved images of joint spaces are provided. More particularly, the present invention utilizes computational image data analysis and processing which provides 3-dimensional images that may be rotated to provide views of joint spaces from any desired point of view, unobstructed by the various joint components, as previously described.

As previously mentioned, the contrast agent composition utilized in the present invention can be comprised of a superpara- or dia-magnetic particulate. Often, contrast agents are toxic and therefore may be coated, including biologically coated. These coatings may be biological coatings and biodegradable. Possible coatings of contrast agent compositions can include dextran, poly-lysine or other polymers, for example. In order to remove the contribution of bone and marrow and tissue, the contrast agent composition utilized in the present invention must make its way into these, as well as other tissues that may be suppressed.

In order for a medically useful image of the joint space to be produced, various methods of tissue suppression may be utilized, dependent on the exact components of the joint region that are to be excluded in the final magnetic resonance image. Components of joints that may be targets of suppression may comprise, not in any particular combination, blood, bone, fatty tissue, water, and cancellous bone and its contents, for example. These and other components of the joint are accessed by the subject's bloodstream. As such, blood pool contrast agent compositions, when administered intravenously to the subject undergoing MRI of joint regions, are subsequently found in such tissues. This provides, with particular MRI parameters that will be discussed in further detail below, a method by which suppression or inclusion of such tissues is achieved.

Marrow and associated tissues, including bone, have made it difficult for medical personnel to construct useful, 3-dimensional images of joint regions, including joint spaces, that are suitable for analysis. In order to suppress these tissues, particular parameters regarding MRI pulse imaging sequences, in conjunction with particular contrast agent compositions that are within the scope and teachings of the present invention and associated methods, are utilized.

An important aspect of contrast agent compositions utilized in the present invention is the particulate size of the contrast agent utilized for imaging. The contrast agent must be of a minimum size so as not to be cleared out by the kidneys too quickly yet remain in the bloodstream long enough so that the contrast agent (particulate) is distributed into the reticuloendothelial system. The reticuloendothelial system is a system of more or less strongly phagocytic cells (macrophages, histiocytes, and microglia) distributed throughout the body, but primarily found in lymph nodes and in blood and lymph sinuses in the liver, spleen, and bone marrow and functions as a defense system. Contrast agent compositions that will localize into the reticuloendothelial system can be from 5 to 40 nanometers in size and preferably 10 to 30 nanometers.

Additionally, contrast agent compositions that are utilized in accordance with the teachings of the present invention may be administered at various dosages. Exemplary dosages of superparamagnetic or diamagnetic contrast agent compositions, including iron oxide blood pool contrast agent compositions, can be from about 1 to 50 mg/kg at concentrations of 2 to 100 mg/ml. Additional, more preferable dosages can be from about 4 to 25 mg/kg of iron at a concentration of about 20 to 40 mg/ml.

Size selection affects the half-life of the injected contrast agent compositions, that is, the time required for half the quantity of the contrast agent composition deposited in the living organism to be metabolized or eliminated by normal biological processes. It is contemplated that contrast agent compositions within the scope and teachings of the present invention will have half-lives between 5 minutes and 10 hours, more preferably at least 30 minutes to two hours.

The above mentioned physical parameters of contrast agent compositions can be achieved, for example, by utilizing methods of manufacture of ferrite particles as described in EP 640350 (Filler, A). This patent describes methods of manufacture and properties of ferrite particles that are particularly well suited for utilization in accordance with the teachings of the present invention and is herein incorporated in its entirety.

In accordance with the teachings of the present invention, combinations of rf pulse sequences are provided, detailed below, that now results in useful MRI joint images. In conjunction with the intravenous administration, or delivery, of the blood pool contrast agent composition described above, the contributions of various joint components to the resulting image can be suppressed. For example, many joints contain fluids in their joint spaces and these fluids may interfere with the construction of the joint image space. Therefore, the utilization of fluid suppression pulse sequences may be employed to limit the contribution of fluids, such as blood vessels and cerebro-spinal fluid in vertebrae, for example, to the joint image generated by joint imaging system 12. One example of such a technique is fluid attenuated, inversion recovery (FLAIR), described in Bydde et al., Comparison of FLAIR Pulse Sequences with Heavily $T_2$ Weighted SE Sequences in MR Imaging of the Brain, 185 RADIOLOGY SUPP. 151 (1992). Under certain imaging parameters, it may be advantageous to have low protein fluids, such as synovial fluids, show up bright. By utilizing $T_2$-weighted imaging, such low protein fluids register as bright signals that may help to visualize the joint space when optimal rf return, or echo, times are selected. These echo times can be from 60 to 150 ms or more preferably 90 to 110 ms, depending on the parameters and objective of the particular image being constructed.

As a result of the administration of the above described blood pool contrast agent compositions, which, by their above detailed physical properties, become distributed in the reticuloendothelial system as well as other locations, the contribution of bone and marrow to the image generated by joint imaging system 12 can be suppressed. As previously mentioned, blood vessels and bone in addition to marrow are blacked out by the pharmaceutical contrast agent composition. This suppression of bone utilizing the blood pool contrast agent described above is hereby referred to as the "black bone" effect.

A known source of interference in MRI images, particularly in bone marrow, is fat. It is considered to be within the scope of the present invention that fat suppression pulse sequences, as described in U.S. Pat. No. 5,560,360 and herein incorporated, for example, are utilized to suppress bone marrow, in addition to fat. For example if a short tau inversion recovery (STIR) sequence of the type described in Atlas et al., STIR MR Imaging of the Orbit, 151 *AM. J. ROENTGEN.* 1025–1030 (1988) or the Dixon technique for fat suppression described in, for example, Dixon et al., Simple Proton Spectroscopic Imaging, 153 *RADIOLOGY* 189–194 (1984) is used, marrow disappears from the image. Another suitable fat suppression technique utilizes the chemical shift selective pulse sequence (CHESS) as described in Haase et al. NMR Chemical Shift Selective Imaging, 30 *PHYS. MED. BIOL.* 341–344 (1985). Other fat suppression sequences as known in the art are also contemplated to be within the scope of the present invention.

Figure 2A:
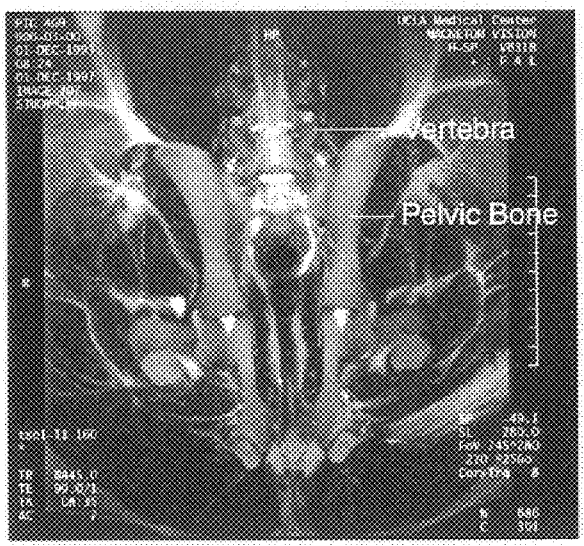
FIG. 2A and 2B are images of porcine pelvic regions. The image of the pelvic region in FIG. 2A is a fat-suppressed, $T_2$ weighted image produced without the administration of a ferrite blood pool contrast agent composition. A superparamagnetic blood pool contrast agent composition is administered to the pig in the image of FIG. 2B, the fat-suppressed, $T_2$ weighted image produced according to the teachings of the present invention.
Figure 2B:
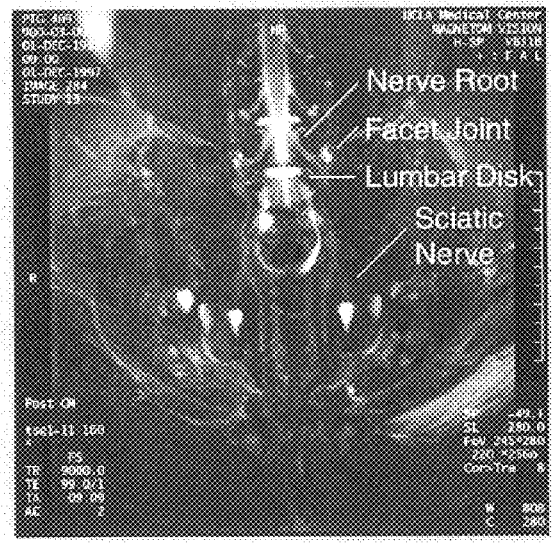

FIGS. 2A and 2B illustrate teachings and methods of the present invention, here, in two magnetic resonance images. In both images, a pig's pelvic region was chosen as a model to demonstrate the teachings and methods of the present invention. In FIG. 2A, the porcine model was imaged utilizing a magnetic resonance scanner. The image of FIG. 2A is a $T_2$-weighted, fat-suppressed image of the pelvic region. As indicated, the vertebrae and pelvic bones are clearly visible. In accordance with the teachings and methods of the present invention, FIG. 2B, another magnetic resonance image, was produced, displaying the aforementioned "black bone" effect. This effect was achieved by the administration of a ferrite blood pool contrast agent composition comprising the previously mentioned physical characteristics which confers localization into the reticuloendothelial system. Consequently, when $T_2$-weighted, fat-suppressed images are produced, the previously conspicuous vertebral and pelvic bones are removed from the image, providing a clear view of the joint region, and in this exemplary image, particularly the lumbar disk and facet joint.

Therefore, by intravenously administering a contrast agent composition of the "blood pool" type displaying the above mentioned physical parameters and collecting fat-suppressed, $T_2$-weighted MRI images, the present invention provides joint region images that are applicable to many diagnostic and therapeutic procedures. In particular, such images provide for 3-dimensional image reconstructions of the joint region. Such 3-D images are rotatable and provided by computational means, such as a computer. This provides views of any angle of the joint space, unobstructed by other joint components such as bone, marrow and blood vessels, for example.

For example, by utilizing the methods and teachings of the present invention, the joint space can be seen in isolation. In order to construct a 3-dimensional image of a joint space, for example, a series of serial, fat-suppressed, $T_2$-weighted images, are stacked and projected onto each other mathematically utilizing a computer to display the resulting 3-dimensional image of the joint space on computer monitor, for example. The collection of fat suppressed, $T_2$-weighted image data and the subsequent image data analysis, to provide useful images, including 3-dimensional images, may be carried out by a myriad of image rendering techniques. Maximum intensity projection is one such 3-dimensional image rendering technique known in the art, that can use serial images produced as a result of the teachings of the present invention. These 3-dimensional, computer rotatable, reconstructions provide an unfettered view of the joint space from any desired perspective. Other surface and volume rendering techniques and software programs, such as fractal imaging, NIH Image and 3-D View for example, wherein 3-dimensional, computer rotatable, reconstructions/images are provided from serial images or data, are also contemplated to be within the scope of the present invention. Furthermore, appropriate software that provides quantitative volume and surface area information of the 3-D rendered image of the joint, may also be utilized. Such quantitative information may be used in diagnostic and therapeutic analysis of the joint region.

Such medically useful images can be utilized in a wide range of applications. For example, joint region images provided by the present invention may be utilized in joint function/loading studies, investigation of pathologies of a joint's cartilage, and to observe the condition of cartilage surfaces. Joint images provided by the present invention can also be utilized to assess post-operative joint fusion procedures as well as evaluating a joint's geometry during range of motion evaluations, for example. The detailed joint region images provided by the present invention may also be utilized to assess the effect of ergonomic designs of tools or furniture, for example, on joint geometry, leading to improved, joint "friendly" designs.

The methods herein disclosed may be utilized in whole-body magnetic resonance apparatus or imagers as well as small body magnetic resonance apparatus or imagers. Small body imagers such as those detailed in U.S. Pat. No. 5,706,813 (Filler, et al.) and incorporated herein by reference, are constructed so as to conform to a particular part of a body, such as a knee or elbow. Advantageously, such an apparatus is constructed with an access port to provide viewing and surgical access to the joint of interest. Utilizing these MRI apparatus and the methods disclosed herein provides "live" joint images that surgeons can utilize during inter-operative procedures at joint regions. That is, the teaching of the present invention allow the joint to be manipulated in "real-time" during surgery, while providing the surgeons with 3-dimensional images and information of the joint region. As mentioned previously, such images are rotatable and provide views of the joint region which are unobstructed by bone, marrow and blood vessels, if so desired.

Therefore the present invention provides surgeons with the ability to employ magnetic resonance images of joints regions with heretofore never achieved accuracy and detail. This provides medical personnel with a diagnostic and therapeutic tool that provides joint images that help in the exact and accurate guidance of surgical tools during inter-operative procedures and diagnostic applications, for example. Accordingly, during internal joint surgery, surgical instrument manipulation will be as accurate as possible, thus reducing peripheral tissue damage. Additionally, with the increase in detail of joint images produced, the likelihood of unnecessary surgery decreases.

It is to be understood that the embodiments of the invention disclosed are illustrative of the principles of the invention. Other modifications may be employed which are within the scope of the invention. Accordingly, the present invention is not limited to that precisely shown and described in the present specification.

I claim:

1. A magnetic resonance apparatus for imaging a joint region, said apparatus comprising:
   a) a polarizing magnetic field source means for exposing said joint region to a polarizing magnetic field;
   b) an excitation and output sensing arrangement means for exposing said joint region to an electromagnetic excitation field;
   c) said output sensing arrangement means having a radio frequency antennae to detect an output response from said joint region, said output response comprising image data;
   d) processor means for processing said output response to:
      (i) process said output response to generate an image representative of said joint region.

2. The apparatus of claim 1, wherein said image data is processed to provide a rotatable 3-D image, which provides viewing of said joint region from any angle to an observer.

3. The apparatus of claim 1, wherein said excitation and output arrangement means is for exposing said joint region to a suppression sequence of electromagnetic fields that suppresses the electromagnetic responsiveness of components in said joint region.

4. The apparatus of claim 3, wherein said suppression sequence is a fat suppression sequence.

5. The apparatus of claim 3, wherein said suppression sequence is a fluid suppression sequence.

6. The apparatus of claim 1, wherein said image data is collected from said joint region where a blood pool contrast agent composition is localized, said image data being $T_2$-weighted, and fat-suppressed.

7. The apparatus of claim 1, wherein said magnetic resonance apparatus is of the whole body type.

8. The apparatus of claim 1, wherein said magnetic resonance apparatus is of the small body type.

9. The apparatus of claim 1, wherein said radio frequency antennae is of the phased array type.

10. The apparatus of claim 1, wherein said image data is $T_2$-weighted.

11. A method for imaging a joint region by magnetic resonance imaging, comprising:
   a) delivering a blood pool contrast agent composition to said joint region;
   b) subjecting said joint region to a polarizing magnetic field;
   c) exposing said joint region to an electromagnetic excitation field;
   d) collecting fat suppressed, $T_2$-weighted image data from said joint region to form images of said joint region, said images comprising a plurality of image data;
   whereby a useful image of said joint region is provided.

12. The method of claim 11, wherein said image data is subjected to image data analysis.

13. The method of claim 12, wherein said image data analysis is 3-dimensional.

14. The method of claim 12, wherein said image data analysis provides a 3-dimensional image of said joint region.

15. The method of claim 14, wherein said 3-dimensional image is displayed on a computer monitor where said 3-dimensional image may be rotated to provide a virtual perspective of said joint region from desired points of view.

16. The method of claim 14, wherein said three dimensional image of said joint space is a maximum intensity projection.

17. The method of claim 11, wherein said joint region is located in a vertebrate animal.

18. The method of claim 17, wherein said blood pool contrast agent composition is injected intravenously into said vertebrate animal.

19. The method of claim 11, wherein said blood pool contrast agent composition is of an iron oxide type.

20. The method of claim 19, wherein said delivery of said iron oxide blood pool contrast agent composition comprises a dose of 1 to 50 mg/kg of iron at a concentration between 2 to 100 mg/ml.

21. The method of claim 19, wherein said delivery of said iron oxide blood pool contrast agent composition comprises a dose of between 4 to 25 mg/kg of iron at a concentration of 20 to 40 mg/ml.

22. The method of claim 11, wherein said blood pool contrast agent is superparamagnetic.

23. The method of claim 11, wherein said blood pool contrast agent is diamagnetic.

24. The method of claim 11, wherein said blood pool contrast agent composition has a half life of five minutes to ten hours.

25. The method of claim 11, wherein said blood pool contrast agent composition has a half life between 30 minutes to two hours.

26. The method of claim 11, wherein said blood pool contrast agent composition is of sufficient size to remain in the bloodstream and be ingested by phagocytic cells in bone marrow.

27. The method of claim 11, wherein said blood pool contrast agent is in the size range of 5 to 40 nanometers.

28. The method of claim 11, wherein said blood pool contrast agent is in the size range of 10 to 30 nanometers.

29. The method of claim 11, wherein said blood pool contrast agent is biodegradable.

30. The method of claim 11, wherein said blood pool contrast agent is biologically coated.

31. The method of claim 30, wherein said biologically coated blood pool contrast agent is dextran coated.

32. The method of claim 11, wherein said magnetic resonance imaging utilizes a polarizing magnetic field between 0.1 to 5 Tesla.

33. The method of claim 11, wherein said magnetic resonance imaging utilizes a polarizing magnetic field between 0.25 to 1.5 Tesla.

34. A method of 3-dimensional imaging of a vertebrate's joint region by magnetic resonance imaging, comprising:
   a) delivering a blood pool contrast agent composition to said joint region;
   b) subjecting said joint region to a polarizing magnetic field;
   c) exposing said joint region to an electromagnetic excitation field;
   d) collecting fat suppressed, $T_2$-weighted image data from said joint region to form 3-dimensional images of said joint region, said 3-dimensional images comprising a plurality of image data;
   whereby a useful 3-dimensional image of said joint region is provided.

35. The method of claim 34, wherein said image data is subjected to image data analysis.

36. The method of claim 35, wherein said image data analysis is comprised of a maximum intensity projection.

37. The method of claim 34, wherein said blood pool contrast agent composition delivery is achieved by intravenous injection into said vertebrate.

38. The method of claim 34, wherein said 3-dimensional image is displayed on a computer monitor where said 3-dimensional image may be rotated to provide a virtual perspective of said joint region from desired points of view.

39. The method of claim 38, wherein said rotatable 3-dimensional image displayed on said computer monitor provides a virtual perspective of said joint region from desired points of view, said points of view of said joint region being unobstructed by extraneous joint region components.

40. The method of claim 39, wherein said extraneous joint region components are comprised of bone, marrow, fat and blood vessels.

\* \* \* \* \*